United States Patent [19]

Saito et al.

[11] Patent Number: 5,312,740
[45] Date of Patent: May 17, 1994

[54] PROCESS FOR PRODUCING TAXOL BY CELL CULTURE OF TAXUS SPECIES

[75] Inventors: Koji Saito; Hiroaki Ohashi; Masaaki Hibi; Makoto Tahara, all of Kawasaki, Japan

[73] Assignee: Nippon Steel Corporation, Tokyo, Japan

[21] Appl. No.: 934,512

[22] PCT Filed: Feb. 10, 1992

[86] PCT No.: PCT/JP92/00132
§ 371 Date: Oct. 9, 1992
§ 102(e) Date: Oct. 9, 1992

[87] PCT Pub. No.: WO92/13961
PCT Pub. Date: Aug. 20, 1992

[30] Foreign Application Priority Data

Feb. 12, 1991 [JP] Japan ................................. 3-019010

[51] Int. Cl.⁵ .......................... C12P 17/02; C12P 1/00; C12N 5/00; C12N 5/02
[52] U.S. Cl. ....................................... 435/123; 435/41; 435/240.4; 435/240.46; 435/240.48; 549/510
[58] Field of Search ..................... 435/41, 123, 240.4, 435/240.46, 240.48; 549/510

[56] References Cited

U.S. PATENT DOCUMENTS 5,019,504  5/1991  Christen et al. .................... 435/123

OTHER PUBLICATIONS

S. H. Mantell et al. (1985) Principles of Plant Biotechnology pp. 91-94.
Christen et al., "Proceedings of the Eightieth Annual Meeting of the American Association for Cancer Research", 30 566(2252)(May 24-27, 1989).

*Primary Examiner*—David T. Fox
*Assistant Examiner*—Bruce R. Campell
*Attorney, Agent, or Firm*—Wenderoth, Lind & Ponack

[57] ABSTRACT

A callus and suspension culture cells containing taxol as an effective component, and a process for producing taxol therefrom, are provided. The callus and suspension culture cells containing taxol in a high content can be induced and proliferated by culturing a tissue of a plant belonging to the genus Taxus, particularly its female gametophyte. The process for cell culture is advantageously carried out in the presence of a particular combination of plant growth regulators known per se in a growth medium. A callus or suspension culture cells containing at least taxol as an effective component can be stably provided, making it possible to effectively produce taxol.

9 Claims, No Drawings

PROCESS FOR PRODUCING TAXOL BY CELL CULTURE OF TAXUS SPECIES

DESCRIPTION

1. Technical Field

The present invention relates to cell culture of plants belonging to the genus Taxus. More specifically, the present invention relates to a process for producing taxol by cell culture of plants belonging to the genus Taxus.

Taxol is an alkaloid of diterpene, which exhibits a carcinostatic activity and inhibits cytokinesis.

2. Background Art

Taxol is a compound promising as an antitumor agent. In particular, for ovarian cancer, taxol has been subjected to the Phase III clinical trial sponsored by the National Cancer Institute (NCI) of National Institute of Health in the U.S.A. In the known process, taxol is produced by an extraction from the bark of the wild Pacific Yew tree, *Taxus brevifolia* NUTT. However, since the Pacific Yew plants grow very slowly, the regrowth of the bark after removal thereof is not expected, and further, the content of taxol therein, and the production efficiency thereof, are very low. For example, as much as 10 tons of the bark are required for producing as little as 1 kg of taxol. Accordingly, it is estimated that 2000 to 4000 Pacific Yew trees, which are 50 to 250 years old, must be cut down to yield 1 kg of taxol. Consequently, many companies and research institutes are attempting to develop alternative processes for producing taxol.

As a substitute for extracting the alkaloid from rare plant sources, there can be mentioned a process for extracting the desired alkaloid from cultured cells from the objective plant tissues grown in an artificial growth medium, but no example of a successful production and/or isolation of taxol from cultured cells of the plant belonging to the genus Taxus has been described in any literature. For example, M. A. Zenkteler et. al. (Acta. Soc. Bot. Pol., 39 (1): pp. 161-173, (1970)) disclose the formation of calli from female gametophytes of *Taxus baccata* LINN., but there is no description of whether or not the disclosed callus formation protocols can be applied to other species of the genus Taxus, and no description of whether or not the calli produce any alkaloid. Also there is no description teaching such matters. Nevertheless, research into the development of processes for producing taxol by cell culture has not been abandoned, since cell culture is still thought to be feasible as a process for producing same.

Therefore, the object of the present invention is, to provide a process for efficiently producing taxol by cell culture of Taxus plant.

DISCLOSURE OF THE INVENTION

To attain the object described above, the present inventors have made intensive research into callus initiation from tissues of plants belonging to the genus Taxus and into proliferation of the callus cells. As a result, it has been found that cultured cells having a high taxol content can be efficiently obtained by culturing specific tissues originating from specific species belonging to the genus Taxus, whereby the present invention was achieved.

Namely, according to the present invention, there is provided a process for producing taxol by culturing cells originating from tissues of plants belonging to the genus Taxus, which comprises:

a) a step of preparing a living tissue;
b) a step of culturing the tissue obtained in step a) in a nutrient medium suitable for inducing a callus, to thereby induce a callus;
c) a step of culturing the callus cells obtained in step b) in a nutrient medium suitable for proliferating suspension culture cells; and
d) a step of recovering taxol from the cultured product obtained in step c).

Also provided are a process for inducing and proliferating the callus using some of the above-described steps, and the callus or suspension culture cells containing at least taxol as an alkaloid.

BEST MODE OF CARRYING OUT THE INVENTION

The phrase "plants belonging to the genus Taxus", as used in the present invention, means plants belonging to the genus Taxus of the family Taxaceae, and suitable for the object of the present invention (i.e. production of taxol). Typical examples thereof include, but are not restricted to, Pacific Yew (*Taxus brevifolia* NUTT.) and Japanese Yew (*Taxus cuspidata* SIEB. et ZUCC.).

According to the present invention, living tissues are prepared from specific tissues of these plants in a first stage. Consequently, as a piece of plant material put into culture, shoots, leaves, roots, flowers, fruits and seeds can be used as it is, or the plant materials may include those prepared in a form suitable for the culture, for example, in the case of the seeds, clean germinating tissues isolated from surface sterilized seeds. Of these, leaves shoots and female gametophytes, which are nutrient-storage tissues of a Gymnosperms seed, are preferable for the present invention. The endosperms or female gametophytes have been hitherto used for studies of tripoid or haploid plant development, and for studies of the bio-synthesis of seed storage nutrients. Surprisingly, the female gametophytes are found particularly suitable for initiating a callus and producing suspension culture cells containing considerable amounts of taxol. The above-described preparation is part of the concept of including treatments in which the plant materials for culture are isolated as they are and alive, and are surface sterilized. Typical examples of such preparations involve, but are not limited to, steps in which, first the materials collected from plants of the genus Taxus are sterilized with 70% ethanol and an aqueous solution of sodium hypochlorite, the raw materials are then aseptically divided into pieces, and thereafter, are transferred onto media solidified by agar or gellan gum suitable for inducing a callus as described hereinbelow.

The living tissues obtained in the above-described stage are then cultured on a nutrient medium suitable for callus induction, and the calli thus derived are transferred to a nutrient medium suitable for the proliferation of callus cells. The primary components to be used in the nutrient media include water; mineral nutrients, e.g. nitrogen (ammonium salts and nitrates), phosphorus, potassium, calcium, magnesium, sulfur, etc.; sugars, e.g., sucrose, glucose, fructose, maltose, etc.; organic substances such as vitamins and amino acids; naturally originating substances such as coconut milk; and optionally, gelling agents, e.g., agar, gellan gum, alginic acid, and agarose. The basic formulations of mineral nutrients known as basic media include Schenk & Hildebrandt medium (hereinafter referred to as "SH medium"), Murashige & Skoog medium (hereinafter referred to as "MS medium"), Gamborg's B5 medium, White's medium, Nitsch & Nitsch medium, Nagata & Takebe medium and woody plant medium. To these basic media are further optionally added auxins such as 1-naphthaleneacetic acid (hereinafter referred to as "NAA"), indole-3-acetic acid (hereinafter referred to as "IAA"), indole-3-butyric acid (hereinafter referred to as "IBA"), and 2,4-dichlorophenoxyacetic acid (hereinafter referred to as "2,4-D"; cytokinins such as benzylaminopurine (hereinafter referred to as "BA"), zeatin, and 6-furfurylaminopurine (kinetin); and gibberellins (hereinafter referred to as "GA" such as $GA_1$ and $GA_3$) as plant growth regulators. As the nutrient media suitable for inducing the callus according to the present invention, media in which auxins, cytokinins and/or gibberellins are added to the above-described basic media are preferable. Typically, a medium using the SH medium as the basic medium to which BA as the cytokinin and $GA_3$ as the gibberellin are added, or to which NAA as the auxin and kinetin as the cytokinin are added, is preferable. On the other hand, as the nutrient media suitable for proliferating suspension culture cells, the above-described basic media with cytokinins and auxins added thereto are used, with the media using the SH medium as the basic medium and having kinetin as the cytokinin and NAA or 2,4-D as the auxin added thereto being particularly preferable. The pH levels of such media are adjusted to 5 to 7, preferably 5.5 to 6.0, with an appropriate acid or alkali.

Each of the above-described cultures using these media can be carried out at a temperature in the range of 15°–25° C. with or without light-irradiatron. In particular, the cultures for the proliferation of the callus cells are preferably carried out in a liquid medium, in which the medium containers are placed on a rotary shaker.

The isolation of taxol thus obtained from the cultured products can be carried out by following the method of extracting various alkaloids from cultured tissue followed by purification, which is known per se. The term "cultured products" used herein is intended to include calli, cultured cells, clumps of cultured cells, cultured tissue, cultured organs and a medium used for the culture. Although not restricted thereto, the taxol can be isolated from such cultivated products by separating calli or cultured cells from media, drying and pulverizing same, extracting taxol from the resulting powder with an appropriate organic solvent, optionally washing the organic phase with water, drying the organic solvent over anhydrous sodium sulfate, magnesium sulfate or calcium chloride, and then evaporating the solvent. If necessary, the taxol thus isolated can be purified by various chromatographic purifications or recrystallization, etc. Examples of an organic solvent which can be used in the extraction include chlorinated hydrocarbons such as methylene chloride and dichloroethane; and alcohols such as methyl, ethyl and isopropyl alcohol.

The substance isolated by the process described above has been confirmed to be taxol, by comparing the NMR, IR, MASS, and UV spectrums thereof with those of a standard sample of taxol received from the above-described NCI.

According to the present invention, the calli or cultured cells having a high taxol content can be effectively obtained by cell culture of the plants belonging to the genus Taxus (for example, about 10 g of cells in dry matter was obtained from a liter of the suspension culture, and the cells thus obtained had a taxol content of 0.05%.) The taxol content of the dried callus was approximately 10 times greater than that of the dried bark of Pacific Yew trees.

The calli or suspension cells containing taxol may be used as an antitumor agent as are, by isolating and pulverizing same.

EXAMPLE

The present invention will now be described in greater detail by referring to working examples, to which the present invention is not restricted.

EXAMPLE 1

A seed (5 g) of *Taxus brevifolia* NUTT from which aril had been removed was immersed in an aqueous solution of 70% W/W ethanol (50 ml) for 10 to 30 seconds, and then in an aqueous sodium hypochlorite solution having an effective chlorine concentration of 1% (50 ml) for 20 minutes, and there after, was rinsed three times in sterile water (100 ml) to eliminate surface contaminants. After the sterilization, the hard external seed coat and the thin internal seed coat were removed with tweezers, and resulting embryos and female gametophytes were then excised and used as an explant.

To prepare medium for culture of an explant obtained as described above, SH medium (supplemented with 0.25% by weight of gellan gum) containing 1, 5 or 10 mg/l of BA as a growth regulator, and having a pH value adjusted to 5.8 with potassium hydroxide or hydrochloric acid, was sterilized by using an autoclave at temperature of 120° C. for 15 minutes, and thereafter, $GA_3$ (separately sterilized by passing through a membrane filter) was added to concentrations of 0, 1, 10 or 100 mg/l. The medium was dispensed into test tubes and solidified, to which the explants were transferred and cultured at a temperature of 20° or 25° C. under a light (16 hours per day), to thus induce in vitro germination of an embryo or callus initiation. It was found that the callus was induced from female gametophytes after approximately 2 months of culture. The results of the callus induction are shown in Table 1.

TABLE 1

| | Results of Culture (Regulator concentration: mg/ml) | | | | | | | |
|---|---|---|---|---|---|---|---|---|
| | 20° C. | | | | 25° C. | | | |
| | $GA_3$ | | | | | | | |
| BA | 0 | 1 | 10 | 100 | 0 | 1 | 10 | 100 |
| 1 | Δ | ○ | Δ | Δ | Δ | ○ | Δ | Δ |
| 5 | Δ | ○ | x | Δ | Δ | ○ | x | x |
| 10 | Δ | ○ | x | x | Δ | ○ | x | x |

○: Initiation and proliferation of callus from female gametophytes
Δ: No initiation of callus
x: Death

EXAMPLE 2

A leaf (5 g) and a shoot (5 g) of *Taxus cuspidata* SIEB. et ZUCC. were immersed in an aqueous solution of 70% W/W ethanol (50 ml) for 15 seconds, and then in an aqueous sodium hypochlorite solution having 1% of an effective chlorine concentration for 10 minutes, and there after, were rinsed three times with sterile water (100 ml) to eliminate surface contaminants. After the sterilization, the leaf and the shoot were cut to lengths of approximately 5 mm.

The explants thus prepared were transferred to MS medium (supplemented with 0.25% by weight of gellan gum) containing NAA and kinetin as plant growth regulators in the concentrations as shown in Tables 2 and 3, and having a pH value adjusted to 5.8 with potassium hydroxide or hydrochloric acid, and were then cultured at a temperature of 20° or 25° C. in the dark or under a light (16 hours per day) to induce a callus. As shown in Table 4, the callus was induced at particular combinations of two plant growth regulator and sucrose concentrations.

TABLE 2

Combinations of Plant Growth Regulator Concentrations in MS Medium Used for Callus Initiation
(Medium containing 30 g/l of sucrose)

| NAA | Kinetin | | |
|---|---|---|---|
|  | 0.5 | 1.5 | 5.0 |
| 1.0 | (1) | (2) | (3) |
| 4.0 | (4) | (5) | (6) |
| 10.0 | (7) | (8) | (9) |

(Regulator concentration Unit: mg/l)
(Number in parentheses indicates medium number used for callus initiation experiments.)

TABLE 3

Combinations of Plant Growth Regulator Concentrations in MS Medium used for Callus Initiation
(Medium containing 10 g/l of sucrose)

| NAA | Kinetin | | |
|---|---|---|---|
|  | 0.0 | 0.1 | 0.5 |
| 1.0 | (10) | (11) | (12) |
| 4.0 | (13) | (14) | (15) |
| 10.0 | (16) | (17) | (18) |

(Regulator concentration Unit: mg/l)
(Number in parentheses indicates medium number used for callus initiation experiments.)

TABLE 4

Results of Callus Induction after 2 months of culture

| Medium No. | Leaf | | Stem | |
|---|---|---|---|---|
|  | Light | Dark | Light | Dark |
| (1) | x | x | o | Δ |
| (2) | x | x | x | x |
| (3) | x | x | x | x |
| (4) | x | x | Δ | x |
| (5) | x | x | o | x |
| (6) | x | x | Δ | x |
| (7) | x | x | x | x |
| (8) | Δ | x | x | x |
| (9) | x | x | x | x |
| (10) | x | x | Δ | x |
| (11) | x | x | x | x |
| (12) | x | x | x | x |
| (13) | x | x | x | x |
| (14) | Δ | x | o | x |
| (15) | x | x | o | x |
| (16) | x | x | x | x |
| (17) | Δ | x | x | x |
| (18) | x | x | x | x | o: Initiation and proliferation of callus
Δ: No initiation of callus
x: Death

EXAMPLE 3

The callus induced from female gametophytes in Example 1 was transferred to SH medium (liquid medium) containing 5 mg/l of NAA and 0, 0.1 or 5 mg/l of kinetin as plant growth regulators and having a pH value adjusted to 5.8. Erlenmeyer 100 ml flasks each containing 40 ml of the medium were used for the culture. The flasks were placed on a rotary shaker and shaken at a rate of 100 rpm, and at a temperature of 20° C., in the dark.

After 4 weeks of culture, it was observed that, in the medium containing 5 mg/l of NAA alone as a growth regulator, the cell mass increased by about 5 times.

Cell growth in the medium containing 5 mg/l of NAA was examined at a temperature of 20° or 25° C. in the dark or under a light (16 hours per day). Although cell mass increased under all test conditions, the largest growth rate was observed at a temperature of 20° C. in the dark.

When 2,4-D was used as the auxin in place of NAA, similar results were obtained.

EXAMPLE 4

The cells grown in Example 3 were collected and air-dried. The extraction and purification of taxol from the cells were carried out with reference to a process for extraction of taxol from the bark of a Taxus plant (M. Keith, *J. Natural Products*, Vol. 53 (5), pp. 1249-1255, 1990). The air-dried cells were pulverized, and extracted with methylene chloride-methanol (1:1). The extraction solution was separated from the cell debris and evaporated, and the residue was then suspended in methylene chloride. This organic suspension was washed with water, and the solvent was then evaporated. The resulting residue was resuspended in methanol, and taxol was isolated and purified from the methanol suspension by High Performance Liquid Chromatography (HPLC) equipped with a reverse phase column (M. Keith, *J. Liquid Chromatography*, Vol. 12, pp. 2117-2132, 1989).

The identification of taxol from the cell culture was carried out by comparing a retention time of peaks obtained for the above-mentioned methanol suspension by HPLC with that of a standard sample of taxol from NCI, and as a result, a peak with an identical retention time with the standard sample was observed. The chemical structure of the substance purified from the methanol suspension by HPLC was determined by a mass spectrum analysis and NMR, and it was confirmed that the substance was taxol. The taxol content was 0.05% of dry matter of suspension cells. This content was larger than that of dried bark by approximately 10 times. (M. Keith, *J. Natural Products*, Vol. 53 (5), pp. 1249-1255, 1990).

EXAMPLE 5

The callus induced from the shoot in Example 2 was transferred to SH medium (liquid medium) containing 5 mg/l of NAA and 0, 0.1, or 5 mg/ml of kinetin as plant growth regulators and having a pH value adjusted to 5.8. Erlenmeyer 100 ml flasks each containing 40 ml of the medium were used for the culture. The flasks were placed on a rotary shaker and shaken at a rate of 100 rpm, and at a temperature of 20° C., in the dark.

After 3 weeks of culture, the callus cells were proliferated only in the medium containing 5 mg/l of NAA alone, at a temperature of 20° C. in the dark.

INDUSTRIAL APPLICABILITY

According to the present invention, callus cells of the Taxus plants containing at least taxol as alkaloids can be effectively induced and proliferated with artificial growth media. Furthermore, taxol can be isolated from these cultured cells. Accordingly, the present invention is available for use in the field of manufacturing medicinal preparations possessing a carcinostatic activity.

We claim:
1. A process for producing taxol by culturing cells originating from tissues of plants belonging to *Taxus cuspidata SIEB. et ZUCC* which comprises:
   a) preparing a living tissue of *Taxus cuspidata*
   b) culturing the tissue obtained in step a) in a nutrient medium containing gibberellin, suitable for inducing a callus, to thereby induce a callus;
   c) culturing the callus cells obtained in step b) in a nutrient medium suitable for proliferating suspension culture cells; and
   d) recovering taxol from the cultured products obtained in step c).

2. The process according to claim 1, wherein the tissue is selected from the group consisting of leaves, shoots and female gametophytes.

3. The process according to claim 1, wherein the cultured product is suspension culture cells.

4. The process according to claim 1, wherein the nutrient medium suitable for inducing the callus is SH medium to which benzyladenine and gibberellin have been added as plant growth regulators.

5. The process according to claim 1, wherein the nutrient medium suitable for proliferating the suspension culture cells is SH medium to which the combination of kinetin with naphthaleneacetic acid or of kinetin with 2,4-dichlorophenoxyacetic acid has been added as plant growth regulators.

6. The process according to claim 1, wherein the nutrient medium suitable for inducing a callus is SH medium to which benzyladenine and gibberellin have been added as plant growth regulators, and the nutrient medium suitable for proliferating the suspension culture cells is SH medium to which the combination of kinetin with naphthaleneacetic acid or of kinetin with 2,4-dichlorophenoxyacetic acid has been added as plant growth regulators.

7. A process for inducing a callus and proliferating suspension culture cells comprising steps of a) to c) of claim 1, a female gametophyte of *Taxus cuspidata* SIEB. et ZUCC. being used as an explant.

8. A callus which contains at least taxol as alkaloids, and obtained by a process comprising the steps of:
   a) preparing a leaf, shoot or female gametophyte of *Taxus cuspidata*; and
   b) culturing the leaf, shoot or female gametophyte obtained in step a) in a medium containing gibberellin suitable for inducing a callus, to thereby induce a callus.

9. Suspension culture cells which contain at least taxol as alkaloids, and obtained by a process comprising the steps of:
   a) preparing a leaf, shoot or female gametophyte of *Taxus cuspidata;*
   b) culturing the leaf, shoot or female gametophyte obtained in step a) in a medium containing gibberellin suitable for inducing a callus, to thereby induce a callus; and
   c) culturing the cells obtained in step b) in a nutrient medium suitable for proliferating suspension culture cells.

* * * * *

UNITED STATES PATENT AND TRADEMARK OFFICE
CERTIFICATE OF CORRECTION

PATENT NO. : 5,312,740
DATED : May 17, 1994
INVENTOR(S) : Toji SAITO et al.

It is certified that error appears in the above-indentified patent and that said Letters Patent is hereby corrected as shown below:

Column 4, line 46, change "mg/ml" to --mg/l--.

Column 6, line 51, change "mg/ml" to --mg/l--.

Signed and Sealed this

Twenty-first Day of May, 1996

Attest:

BRUCE LEHMAN

Attesting Officer      Commissioner of Patents and Trademarks